(12) United States Patent
Hepworth Thompson et al.

(10) Patent No.: US 6,197,763 B1
(45) Date of Patent: Mar. 6, 2001

(54) USE OF METAL COMPLEXES TO TREAT GASTROINTESTINAL INFECTIONS

(75) Inventors: Richard Paul Hepworth Thompson; Jonathan Joseph Powell; Rosemary Helen Phillips, all of London; Sylvaine Francoise Aline Chevalier, Surbiton, all of (GB)

(73) Assignee: Pflori Limited, London (GB)

( * ) Notice: Subject to any disclaimer, the term of this patent is extended or adjusted under 35 U.S.C. 154(b) by 0 days.

(21) Appl. No.: 09/284,217

(22) PCT Filed: Oct. 10, 1997

(86) PCT No.: PCT/GB97/02797

§ 371 Date: Aug. 30, 1999

§ 102(e) Date: Aug. 30, 1999

(87) PCT Pub. No.: WO98/16218

PCT Pub. Date: Apr. 23, 1998

(30) Foreign Application Priority Data

Oct. 11, 1996 (GB) .................................................. 9621273

(51) Int. Cl.[7] .................................................. A61K 31/555
(52) U.S. Cl. .......................... 514/184; 424/630; 424/638; 424/639; 424/643; 424/646; 514/675; 514/682
(58) Field of Search .................................. 514/184, 682, 514/675; 424/630, 638, 639, 643, 646

(56) References Cited

U.S. PATENT DOCUMENTS

| 4,575,502 | 3/1986 | Hider et al. . |
| 4,585,780 | 4/1986 | Hider et al. . |
| 4,665,064 | 5/1987 | Hider et al. . |
| 4,834,983 | 5/1989 | Hider et al. . |
| 4,861,767 | 8/1989 | Hider et al. . |

FOREIGN PATENT DOCUMENTS

| 0 159 917 | 4/1985 | (EP) . |
| 0 159 194 | 10/1985 | (EP) . |
| 0 454 449 A1 | 4/1991 | (EP) . |
| 0 445 949 A1 | 9/1991 | (EP) . |
| 03067565 | of 1991 | (JP) . |
| WO 95/25513 | 3/1994 | (WO) . |
| WO 96/41627 | 12/1996 | (WO) . |

OTHER PUBLICATIONS

Vicari et al, Acta Endoscopica, 25(3), 275–277, 1995.*
*Letters in Applied Microbiology*, 1996, 22; pp. 189–191; F. Schved et al.; "Sensitization of *Escherichia coli* to nisin by maltol and ethyl maltol".

*Department of Chemistry, Islamia University*; vol. 3, No. 5, 1996; pp. 217; Zahid Hussain Chohan et al.; Pharmacological Role of Anions (Sulphate, Nitrate, Oxalate and Acetate) on the Antibacterial Activity of Cobalt(II) Copper(II) and Nickel(II) Complexes with Nicotinoylhydrazine–Derived Ono, NNO and SNO Ligands.
*Bull. Environ. Contam. Toxicol.*, (1984) 33; pp. 114–120; G. A. Thompson et al.; Comparative Study of the Toxicity of Metal Compounds to Heterotrophic Bacteria.
*J. Dent. Res.*; Jan. 1993; pp. 25–30; D. J. Bradshaw et al.; "The Effects of Triclosan and Zinc Citrate, Alone and in Combination, on a Community of Oral Bacteria Grown In vitro".
*Diagn Microbiol Infect Dis*; 1992; 15; pp. 549–552; Nai–xun Chin et al.; "The Activity of Metal Compounds Against Aerobic and Anaerobic Bacteria".
*Gastroenterology* 1990;99; pp. 863–875; Gorbach, "Bismuth Therapy in Gastrointestinal Diseases".
*Aliment. Pharmacol. Therap* (1990) 4, pp. 163–169; C.U. Nwokolo et al.; "The absorption of bismuth and salicylate from oral doses of Pepto–Bismol (bismuth salicylate)".
*The Medical Journal of Australia*; vol. 142, Apr. 15, 1985; pp. 439–444; Barry J. Marshall et al.; "Pyloric campylobacter infection and gastroduodenal disease".
*European Journal of Clinical Investigation* (1991) 21; pp. 551–557; M. Nilius et al.; "In vitro inhibition of *Helicobacter pylori* urease: biochemical and ultrastructural analysis".
*Infection and Immunity*, Jan. 1994; vol. 62, No. 1; pp. 299–302; Guillermo I. Perez–Perez et al.; "Effects of Cations on *Helicobacter pylori* Urease Activity, Release, and Stability".
*Gastroenterology*, vol. 114, No. 4; Polaprezinc (7–103); AGA; Abstract A 139 (Apr. 1995); Hajime Kuwayama.
*FEMS Microbiology Immunology*, 47 (1988); pp. 55–60; J. H. Brock et al.; "The effect of synthetic iron chelators on bacterial growth in human serum".
*Clinical Microbiology Reviews*, Jan. 1990, p. 1–12, George S. Buck, "Campylobacter pylori and Gastroduodenal Disease".

\* cited by examiner

*Primary Examiner*—Rebecca Cook
(74) *Attorney, Agent, or Firm*—Kilpatrick Stockton, LLP

(57) ABSTRACT

Novel dietary complexes for gastrointestinal symptoms and gastrointestinal microbes are provided. They comprise a dietary metal and a dietary ligand wherein the dietary metal is selected from zinc, copper, cobalt, manganese and iron and the dietary ligand is lawsone or tropolone.

17 Claims, No Drawings

USE OF METAL COMPLEXES TO TREAT GASTROINTESTINAL INFECTIONS

This is a 371 of PCT/GB97/02797 filed Oct. 10, 1997.

The present invention relates to novel therapies to treat gastrointestinal symptoms and gastrointestinal microbes. In particular, therapies are provided for common gastrointestinal symptoms such as dyspepsia and non-infectious diarrhoea and for common gatrointestinal infections such as *Helicobacter pylori* and Salmonella. The use of complexes of dietary metals in preparing therapeutic agents for use in such methods is also provided.

Gastrointestinal infections cause widespread diarrhoea and debility and account for a large proportion of antibiotic use worldwide. The non-specificity of antibiotics has meant that resistant pathogens are an increasing problem leading to more complex treatments. Furthermore, many antibiotics have side effects that reduce compliance, while cost may preclude their use in developing countries where infections are more common. Even in the western world complex treatment is often required, for example, *H. pylori* infection of the gastric mucosa requires "triple therapy" for successful eradication. There are however few gut-specific antimicrobials and antibiotics designed for absorption and systemic action are mainly used.

Toxic metal compounds have been in use for some considerable time in the treatment of gastrointestinal symptoms and of gastrointestinal and even systemic infections, but significant side effects occur, such as the encephalopathy seen with bismuth complexes (Gorbach S. L., *Gastrenterology*, 99:863–875 (1990)). Newer "colloidal" bismuth compounds such as De-Noltab™ (bismuth subcitrate) and Pepto-Bismol™ (bismuth sub-salicylate) are not well absorbed in man and have some activity against gastrointestinal bacteria. However, it has been shown that significant and prolonged plasma levels of bismuth are found following ingestion of such preparations (Nwokolo et al, *Alimentary, Pharmacology and Therapeutics*, 4:163–169 (1990)) (up to 135 $\mu$g/l for De-Noltab™ and 5 $\mu$g/l for Pepto-Bismol™).

These earlier metal-based therapies in the gastrointestinal tract have, unknowingly, been mainly effective against gastrointestinal pathogens due to their physiological effects on the gut, rather than due to any antimicrobial properties, as unlike in vitro, sufficient concentrations of bismuth appear not to reach the bacteria in vivo. This has been confirmed by work we have carried out on the therapeutic role of bismuth compounds in the eradication of *H. pylori*.

In view of the effectiveness, but potential toxic effects, of bismuth we have looked at "dietary metals" as possible treatments for gastrointestinal symptoms and infections. These metals, unlike bismuth, form part of normal dietary requirements and therefore, firstly it is not necessary to ensure that minimal absorption of the metal-ion takes place, while secondly normal homeostatic mechanisms in higher animals will regulate the metal absorption. In order to improve their antimicrobial efficacy the dietary metals can be complexed with ligands.

One example of a microbial infection treatable by the methods described herein is that cused by *H. pylori*. *H. pylori* is a Gram negative bacteria that has been strongly implicated in chronic active gastritis and peptic ulcer disease (Marshall et al, *Medical Journal of Australia*, 142:439–444 (1985); Buck, G. E., *Journal of clinical Microbiology*, 3:1–12 (1990)). More recently, it has also been implicated in the development of gastric cancer and lymphoma. As mentioned above, H.pylori infection is one example where complex triple therapies are required for eradication. One example is based on omeprazole™ (20 mg b.d.) with amoxycillin (500 or 750 mg t.d.s.) and metronidazole (400 mg t.d.s.). It would be particularly useful therefore to have available a simpler, less expensive therapy with good eradication rates.

We have now found that the use of complexes of dietary metal ions optionally together with one or more antibiotics and/or other therapeutic agents represent an effective therapeutic method for the eradication of gastrointestinal microbes and improvement of gastrointestinal symptoms in vivo. For example, for infections caused by *H. pylori* the dietary metal complexes can be used in conjunction with antibiotic(s) and/or agents such as proton pump inhibitors (eg omeprazole™).

Thus, in a first aspect, the present invention provides a method of treating gastrointestinal symptoms or gastrointestinal microbes in a mammal which comprises the step of administering orally or rectally to a subject an effective amount of a complex of at least one dietary metal ion.

In the context of the present invention "dietary metal" means a metal that forms part of normal dietary requirements for mammals, eg humans. In the case of humans examples of such dietary metals include zinc, copper, cobalt, manganese and iron. Preferred dietary metal ions include zinc, copper, manganese and iron.

The "complex" will comprise the dietary metal ion and at least one form of counter ion. Particularly suitable counter ions include ligands of relatively low molecular weight being either common dietary ligands or natural or synthesised ligands. It will be apparent to the skilled man that the "complex" could be formed in situ by separately administering a salt of a dietary metal and one or more suitable ligands. Thus, methods based on separate administration of dietary metal salts and ligands fall within the scope of the invention.

Therefore the methods of the invention make use of common dietary metals and thus avoid the problems associated with therapies based on foreign metals such as bismuth.

Examples of suitable dietary ligands that form complexes with the dietary metals include ascorbate, aspartate, citrate, histidine, malate, maltol (3-hydroxy-2-methyl-4-pyrone), gluconate, glutamate, glutamine, succinate and tartrate. Preferred dietary ligands include ascorbate, citrate, histidine, malate, maltol (3-hydroxy-2-methyl-4-pyrone), gluconate and tartrate. Examples of other ligands include lawsone (2-hydroxy-1,4-napthoquinone) and tropolone (2-hydroxy-2,4,6-cycloheptatrienone). The ligand used could also be an antibiotic itself or any other suitable compound. For example, in the case of *H. pylon* infection, metal-ion pump inhibitors or urease inhibitors can be used as the ligand. Suitable ratios of metal:ligand fall in the range 1:1 to 1:10.

In one embodiment the complex is administered orally.

There is available on the market in the UK a proprietary product, which is marketed as a dietary supplement which provides zinc. The product is listed as a zinc sulphate preparation. However, the product is first dissolved in water before being taken orally. When it is dissolved a zinc citrate complex (citrate also being present in the formulation) is formed with three citrate ions for each zinc ion. Thus, such a product can be used in the methods of the present invention as a source of zinc citrate.

*H. pylori* infection represents one form of gastrointestinal infection which can be treated using the methods of the invention and thus, methods of treating *H. pylori* infection form an embodiment of the invention. In a preferred embodiment of the invention the dietary metal/counter ion complex is administered in combination with one or more antibiotics, eg amoxycillin or metronidazole. In a particularly preferred embodiment for the treatment of *H. pylori* infections the dietary metal complex is administered with at least one antibiotic and/or another compound which is used in conventional ulcer treatments and/or which is used to treat gastrointestinal symptoms/infections. Such compounds include ranitidine™, which is an $H_2$ receptor antagonist, and proton pump inhibitors such as omeprazole™.

Although, in preferred embodiments, the methods of the present invention will be used to treat humans, it will be appreciated that they will be equally applicable as veterinary treatments of gastrointestinal symptoms and/or infections in animals, eg swine dysentry.

In a second aspect the present invention provides a pharmaceutical formulation for use in the treatment of gastrointestinal symptoms and/or gastrointestinal microbes comprising a complex of at least one dietary metal, other than a complex of zinc and citrate, optionally together with one or more pharmaceutically acceptable carriers, excipients and/or diluents.

In a third aspect the present invention provides a pharmaceutical formulation comprising at least one salt of a dietary metal, other than zinc sulphate, and at least one ligand optionally together with one or more pharmaceutically acceptable carriers, excipients and/or diluents.

Optionally, the pharmaceutical formulations of the invention may also contain one or more additional therapeutic agents, eg one or more antibiotics, $H_2$ receptor antagonists and/or proton pump inhibitors.

For the methods of the present invention a dose of up to 50 mg metal/kg/day for humans and up to 500 mg/kg/day for animals may be used. Preferably, the daily dose will be up to 10 mg/kg for humans and up to 100 mg/kg for animal use. In all cases, precise dosage will depend on the condition being treated and the age, weight and condition of the patient or animal as well as the route of administration. The pharmaceutical formulations of the invention may be presented in unit dose forms containing a predetermined amount of active ingredient per dose. This predetermined dose may either be the whole daily dose or a suitable sub-dose thereof. Thus, for example in humans, such a unit may be adapted to provide up to 25 mg/kg/day of metal and consequently the patient may be required to take two such sub-doses.

For use in the methods of the present invention the pharmaceutical formulations will be adapted for administration by the oral (including buccal or sublingual) or rectal route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

In addition, pharmaceutical formulations may be used which provide particular release profiles of the complex. This may be particularly advantageous in targeting the complex to a particular part of a subject's digestive system. Thus, for example, it is possible to formulate the complex as a colonic delivery system. Such systems are readily available and would be well known to the skilled person.

Other types of formulations which may be useful include those which have particular release profiles based on pH, time or the presence of particular bacteria. Again, these types of formulation are well known to the skilled person.

Pharmaceutical formulations adapted for rectal administration may be presented as suppositories or enemas.

Preferred unit dosage formulations are those containing a daily dose or sub-dose, as herein above recited, or an appropriate fraction thereof, of an active ingredient.

It should be understood that in addition to the ingredients particularly mentioned above, the formulations may also include other agents conventional in the art, for example the formulations may include flavouring agents.

In a fourth aspect the present invention provides the use of a complex of at least one dietary metal in the preparation of a medicament for the treatment of a gastrointestinal symptoms and/or gastrointestinal microbes.

In a fifth aspect the present invention provides the use of a salt of at least one dietary metal and at least one ligand in the preparation of a medicament for the treatment of gastrointestinal symptoms and/or gastrointestinal microbes.

In a sixth aspect the present invention provides a product comprising a salt of at least one dietary metal and at least one ligand as a combined preparation for simultaneous, separate or sequential use in the treatment of gastrointestinal symptoms and/or gastrointestinal microbes.

In a seventh aspect the present invention provides a product comprising a salt of at least one dietary metal and at least one ligand as a combined preparation for simultaneous, separate or sequential use in the treatment of *H. pylori* infection.

In one embodiment of the sixth and seventh aspects of the invention the product additionally comprises at least one additional therapeutic agent, for example an antibiotic, $H_2$ receptor antagonist and/or proton pump inhibitor.

In an eighth aspect the present invention provides a product comprising a complex of at least one dietary metal and at least one antibiotic as a combined preparation for simultaneous, separate or sequential use in the treatment of gastrointestinal symptoms and/or gastrointestinal microbes.

In a ninth aspect the present invention provides a product comprising a complex of at least one dietary metal and at least one antibiotic as a combined preparation for simultaneous, separate or sequential use in the treatment of *H. pylori* infection.

In one embodiment of the eighth and ninth aspects of the invention the product may further comprise at least one additional therapeutic agent, for example a $H_2$ receptor antagonist and/or a proton pump inhibitor.

Preferred features of each aspect of the invention are applicable to each other aspect *mutatis mutandis*.

The invention will now be described by reference to the following examples which should not be construed as in any way limiting the invention.

EXAMPLE 1

Study Of *H. pylori* Eradication Using Metal Based Therapies

In Vitro Minimum Inhibitory Concentrations (Mics) Using Metal-Ligand Complexes

| | MIC against *H. pylori* (µg/l) |
|---|---|
| Zinc Salt | >>64 |
| Citrate | >>64 |
| Zinc Citrate | 8–64 |

In vivo: Eradication of *H. Pylori* Infection in Man Using Metal Based Therapies 104 *H. pylori* positive patients were treated with one of five different treatment regimes over a period of two weeks. The treatments were as follows:
1. AM regime: Amoxycillin (500 mg tds)+metronidazole (400 mg tds)
2. DAM regime: De-Noltab (1 tablet qds)+amoxycillin (500 mg tds)+metronidazole (400 mg tds)
3. ZAM regime: Zinc citrate (200 mg tds)+amoxycillin (750 mg tds)+metronidazole (400 mg tds)
4. ZSO$_4$AM regime: Zinc sulphate (220 mg tds)+ amoxycillin (750 mg tds)+metronidazole (400 mg tds)
5. FAM regime: Ferric maltol (233 mg bd)+amoxycillin (500 mg tds)+metronidazole (400 mg tds)

| Treatment regime | n = | Eradication of H.pylori | Lost to follow up | % Eradication |
|---|---|---|---|---|
| AM | 35 | 10 | 1 | 28 |
| DAM | 35 | 24 | 1 | 69 |
| ZAM | 12 | 9 | 0 | 75 |
| ZSO$_4$AM | 12 | 3 | 0 | 25 |
| FAM | 10 | 5 | 0 | 50 |

A = amoxycillin, M = metronidazole, D = De-Noltab (colloidal bismuth citrate, Z = Zinc citrate, ZSO$_4$ = Zinc sulphate, F = Ferric (maltol)$_3$ Discussion It can be seen that the zinc citrate regime (ZAM) showed a significant eradication rate (75%). For the remaining patients in this group non-compliance was indicated. This eradication rate is significantly better is than antibiotics alone (amoxycillin plus metronidazole: 28%) and is similar to the eradication rate achieved with standard bismuth based tripl therapy in our community (DAM=69%).

The zinc sulphate regime (ZSO$_4$AM) gave an eradication rate of only 25% which is only as good as the antibiotics alone suggesting that zinc sulphate had no additional benefit over the antibiotics.

The ferric maltol regime (FAM) gave an eradication rate of 50% which is better than antibiotics alone but not as effective as the zinc citrate regime (ZAM), although formulation of the ferric maltol has not been optimised. Thus, the use of dietary metal complexes should lead to effective, simpler treatments for *H. pylon* infection.

EXAMPLE 2

Study of MICs of Other Metal-Ligands Against *H. pylori*

| Metal-ligand complex | MIC (µg/l) |
|---|---|
| Iron-tropolone | 0.5–1 |
| Metal-lawsone complexes | 0.016–1 |
| Metal-tetracycline complexes | 0.008–0.125 |

What is claimed is:

1. A method of treating a gastrointestinal symptom, a gastrointestinal bacterial infection, or a combination thereof, in a mammal which comprises administering to the mammal an effective amount of a therapeutic complex comprising a dietary metal and a dietary ligand, wherein the dietary metal is selected from the group consisting of zinc, copper, cobalt, manganese and iron and the dietary ligand is lawsone (2-hydroxy-1,4,napthoguinone) or tropolone (2-hydroxy-2,4,6-cycloheptatrienone).

2. The method of claim 1, wherein the dietary metal is selected from the group consisting of copper, manganese and iron.

3. The method of claim 1, wherein the ratio of dietary metal: dietary ligand in the therapeutic complex is in the range 1:1 to 1:10.

4. The method of claim 1, wherein the therapeutic complex is administered orally or rectally.

5. The method of claim 1, wherein the gastrointestinal bacterial infection is caused by a strain of *Heliobacter pylori*.

6. The method of claim 1, wherein the therapeutic complex is formed in situ by separate administration of a dietary metal salt, and a dietary ligand.

7. The method of claim 1, wherein the therapeutic complex is administered simultaneously or sequentially with at least one additional therapeutic agent.

8. The method of claim 7, wherein the additional therapeutic agent is an antibiotic, an H$_2$ receptor antagonist, or a proton pump inhibitor, or a combination thereof.

9. A composition for use in the treatment of a gastrointestinal bacterial infection, comprising a complex of a ligand and a dietary metal selected from the group consisting of zinc, copper, cobalt, manganese, and iron, or a salt thereof, wherein the ligand is lawsone (2-bydroxy-1,4, napthoquinone) or tropolone (1-hydroxy2,6-cycloheptatrienone), optionally combined with a pharmaceutically acceptable carrier or diluent.

10. The composition of claim 9, wherein the dietary metal is selected from the group consisting of copper, manganese, and iron.

11. The composition of claim 9, further comprising a therapeutic agent, wherein the therapeutic agent is selected from the group consisting of an antibiotic, an H$_2$ receptor antagonist, and a proton pump inhibitor, or a combination thereof.

12. A composition, comprising a dietary metal salt and a ligand for simultaneous, separate or sequential use in the treatment of a gastrointestinal symptom, a gastrointestinal bacterial infection, or a combination thereof, wherein the dietary metal is selected from the group consisting of zinc, copper, cobalt, manganese and iron, and wherein the ligand is lawsone (2-hydroxy-1,4,napthoguinone) or tropolone (2-hydroxy-2,4,6-cycloheptatrienone).

13. The composition of claim 12, for simultaneous use, wherein the dietary metal is complexed with the ligand.

14. The composition of claim 12, further comprising a pharmaceutically acceptable carrier or diluent.

15. The composition of claim 12, wherein the dietary metal is selected from the group consisting of copper, manganese and iron.

16. The composition of claim 12, wherein the ratio of the dietary metal salt to ligand in the complex is in the range of 1:1 to 1:10.

17. The composition of claim 12, further comprising a therapeutic agent, wherein the therapeutic agent is selected from the group consisting of an antibiotic, an H$_2$ receptor antagonist, and a proton pump inhibitor, or a combination thereof.

* * * * *

UNITED STATES PATENT AND TRADEMARK OFFICE
CERTIFICATE OF CORRECTION

PATENT NO. : 6,197,763 B1  
DATED : March 6, 2001  
INVENTOR(S) : Richard Paul Hepworth Thompson; Jonathan Joseph Powell; Rosemary Helen Phillips; Sylvaine Francoise Aline Chevalier Page 1 of 1

It is certified that error appears in the above-identified patent and that said Letters Patent is hereby corrected as shown below:

Title page,

Section 12,
Please change the name to read -- Thompson et al. --

Signed and Sealed this

Thirtieth Day of October, 2001

Attest:

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

| | |
|---|---|
| PATENT NO. | : 6,197,763 B1 |
| DATED | : March 6, 2001 |
| INVENTOR(S) | : Richard Paul Hepworth Thompson, Jonathan Joseph Powell, Rosemary Helen Phillips, Sylvaine Francoise Aline Chevalier |

It is certified that error appears in the above-identified patent and that said Letters Patent is hereby corrected as shown below:

<u>Title page,</u>
Item [73], change the name of the Assignee to read -- Pfylori Limited --.

Signed and Sealed this

Twenty-seventh Day of August, 2002

*Attest:*

*Attesting Officer*

JAMES E. ROGAN
*Director of the United States Patent and Trademark Office*